United States Patent
Poulet et al.

(10) Patent No.: US 6,534,066 B1
(45) Date of Patent: Mar. 18, 2003

(54) INACTIVATED VACCINE AGAINST FELINE CALICIVIROSIS

(75) Inventors: Herve Poulet, Lyons (FR); Sylvian Gabriel Goutebroze, Lyons (FR)

(73) Assignee: Merial, Lyons (FR)

( * ) Notice: Subject to any disclaimer, the term of this patent is extended or adjusted under 35 U.S.C. 154(b) by 0 days.

(21) Appl. No.: 09/616,781

(22) Filed: Jul. 14, 2000

Related U.S. Application Data

(60) Provisional application No. 60/193,197, filed on Mar. 30, 2000.

(30) Foreign Application Priority Data

Jul. 16, 1999 (FR) .............................................. 99 09420
Feb. 11, 2000 (FR) ............................................ 00 01759

(51) Int. Cl.$^7$ ........................................... A61K 39/125
(52) U.S. Cl. .................. 424/216.1; 424/93.2; 424/93.3; 424/93.6; 424/185.1; 424/196.11; 435/173.1; 435/236; 435/237; 435/239
(58) Field of Search ............................... 424/93.2, 93.3, 424/93.6, 185.1, 196.11, 216.11; 435/173.3, 236, 237, 239

(56) References Cited

U.S. PATENT DOCUMENTS 3,937,812 A * 2/1976 Bittle et al. .................... 424/89
5,716,822 A * 2/1998 Wardley et al. .......... 435/235.1

FOREIGN PATENT DOCUMENTS

WO    WO 98/56929    12/1988

OTHER PUBLICATIONS

Geissler et al. Feline calicivirus capsid protein expression and capsid assembly in cultures feline cells. Journal of Virology (1999) vol. 73, No. 1, pp. 834–838.*

Poulet et al., Database Medline Online, U.S. National Library of Medicine (NLM), "Comparison between acute oral/respiratory and chronic stomatitis/gingivitis isolates of feline calicivirus: pathogenicity, amtigenic profile and cross-–neutralization studies", Arhives of Virology (2000) 145 (2) 243–61, XP002138104.

* cited by examiner

*Primary Examiner*—James Housel
*Assistant Examiner*—Ulrike Winkler
(74) *Attorney, Agent, or Firm*—Frommer Lawrence & Haug LLP; William S. Frommer; Thomas J. Kowalski

(57) ABSTRACT

Immunogenic preparations and vaccines, in particular which are inactivated, effective against feline calicivirosis, based on an FCV virus strain 431 as deposited at the CNCM under the accession number CNCM I-2166, or one of its equivalents, in a veterinarily acceptable vehicle or excipient, preferably combined with FCV virus obtained from another FCV strain, in particular strain G1 as deposited at the CNCM under the accession number CNCM I-2167.

11 Claims, 2 Drawing Sheets

| Isolate/serum | SrA2 | SrF1 | SrG1 | SrH3-2 | SrG3 | SrF30-31 | SrH1-4 | Sr388b | Sr431 | Sr337 | SrJ5 | SrRMI1 | SrRMI2 | SrRMI3 | SrRMI5 | SrRMI6 | SrRMI7 | SrRMI9 | Sr255 | SrF9 |
|---|---|---|---|---|---|---|---|---|---|---|---|---|---|---|---|---|---|---|---|---|
| A2 (FR) | 3.5 | 0.8 | 2.5 | 1.2 | 1.0 | 1.8 | 1.3 | 0.7 | 0.8 | 1.1 | 0.9 | 0.7 | 0.7 | 0.7 | 2.0 | 1.2 | 0.7 | 1.7 | 1.2 | 1.8 |
| F1 (FR) | 1.2 | 3.0 | 2.2 | 1.9 | 0.9 | 1.1 | 1.0 | 1.9 | 1.3 | 0.7 | 0.7 | 0.7 | 0.7 | 0.7 | 0.7 | 0.7 | 0.7 | 0.7 | 0.7 | 1.0 |
| G1 (FR) | 1.6 | 0.8 | 2.9 | 1.2 | 1.0 | 1.7 | 0.7 | 0.9 | 2.6 | 0.7 | 0.8 | 1.1 | 0.7 | 0.7 | 0.9 | 0.7 | 0.7 | 0.7 | 1.3 | 1.1 |
| H3-2 (FR) | 0.7 | 0.7 | 0.7 | 2.8 | 0.7 | 0.7 | 0.9 | 0.8 | 1.3 | 0.7 | 1.1 | 0.7 | 0.7 | 0.7 | 0.7 | 0.7 | 0.7 | 0.7 | 0.7 | 0.7 |
| G3 (FR) | 1.0 | 1.1 | 2.4 | 1.7 | 3.5 | 1.6 | 1.3 | 0.9 | 1.8 | 0.7 | 0.7 | 1.1 | 0.7 | 0.7 | 0.7 | 0.7 | 0.7 | 0.7 | 0.8 | 0.7 |
| F3031 (FR) | 2.4 | 1.5 | 2.0 | 1.7 | 1.2 | 3.8 | 1.1 | 1.2 | 2.0 | 0.7 | 1.2 | 0.8 | 0.7 | 0.7 | 0.7 | 1.0 | 0.7 | 1.2 | 1.1 | 2.0 |
| H1-4 (FR) | 0.7 | 0.7 | 1.1 | 1.2 | 0.7 | 0.7 | 3.2 | 0.7 | 1.3 | 0.7 | 1.0 | 0.7 | 0.7 | 0.7 | 0.7 | 1.1 | 0.7 | 0.7 | 0.7 | 0.7 |
| 388b (UK) | 0.7 | 0.7 | 0.7 | 0.7 | 0.7 | 0.7 | 0.7 | 3.3 | 2.1 | 0.7 | 0.9 | 0.7 | 0.7 | 0.7 | 0.7 | 0.7 | 0.7 | 0.7 | 0.7 | 0.7 |
| 431 (UK) | 0.7 | 0.7 | 0.9 | 0.7 | 0.7 | 0.8 | 0.8 | 1.3 | 3.5 | 1.0 | 1.2 | 0.7 | 0.7 | 0.7 | 0.7 | 0.7 | 0.7 | 0.7 | 0.8 | 0.7 |
| 337 (UK) | 1.0 | 0.7 | 1.1 | 0.7 | 0.7 | 0.9 | 1.1 | 1.2 | 2.2 | 3.2 | 1.2 | 0.7 | 0.7 | 0.7 | 0.7 | 0.7 | 1.0 | 0.7 | 0.9 | 0.7 |
| J5 (UK) | 0.7 | 0.7 | 1.0 | 0.7 | 0.7 | 0.7 | 1.1 | 0.8 | 1.6 | 0.7 | 3.3 | 0.7 | 0.7 | 0.7 | 0.8 | 0.7 | 0.7 | 0.7 | 0.7 | 0.7 |
| RMI1 (US) | 0.7 | 0.7 | 1.0 | 1.2 | 0.7 | 0.7 | 0.7 | 1.1 | 1.6 | 0.7 | 1.0 | 2.7 | 2.3 | 0.7 | 0.7 | 1.0 | 1.3 | 0.7 | 0.7 | 0.7 |
| RMI2 (US) | 0.7 | 0.7 | 1.0 | 0.7 | 0.7 | 0.7 | 0.7 | 0.7 | 1.4 | 0.7 | 1.3 | 0.7 | 2.2 | 3.1 | 0.7 | 1.3 | 1.3 | 1.8 | 0.7 | 0.7 |
| RMI3 (US) | 0.7 | 0.7 | 1.2 | 0.7 | 0.7 | 0.7 | 0.7 | 1.3 | 1.5 | 1.8 | 1.0 | 2.6 | 2.2 | 0.7 | 2.0 | 1.3 | 1.8 | 1.2 | 0.8 | 0.7 |
| RMI5 (US) | 1.2 | 0.7 | 1.1 | 0.7 | 0.7 | 0.7 | 0.7 | 1.5 | 1.9 | 0.7 | 0.9 | 0.8 | 1.2 | 0.7 | 2.4 | 1.3 | 0.7 | 0.7 | 0.9 | 0.7 |
| RMI6 (US) | 1.2 | 0.7 | 1.2 | 0.7 | 0.7 | 1.3 | 1.3 | 0.7 | 1.0 | 0.7 | 1.4 | 1.1 | 1.2 | 0.7 | 0.7 | 2.5 | 0.7 | 2.5 | 0.7 | 0.7 |
| RMI7 (US) | 1.1 | 0.7 | 1.1 | 0.7 | 0.7 | 0.7 | 0.7 | 0.7 | 1.8 | 0.7 | 0.7 | 0.7 | 0.7 | 0.7 | 0.8 | 0.7 | 3.0 | 0.7 | 0.7 | 0.7 |
| RMI9 (US) | 1.1 | 0.7 | 1.2 | 0.7 | 0.9 | 0.7 | 1.3 | 0.7 | 1.0 | 0.7 | 0.7 | 0.7 | 0.7 | 0.7 | 0.7 | 2.5 | 0.7 | 2.4 | 0.7 | 0.7 |

FIGURE 1: NEUTRALIZING TITERS OBTAINED DURING CROSS-NEUTRALIZATIONS

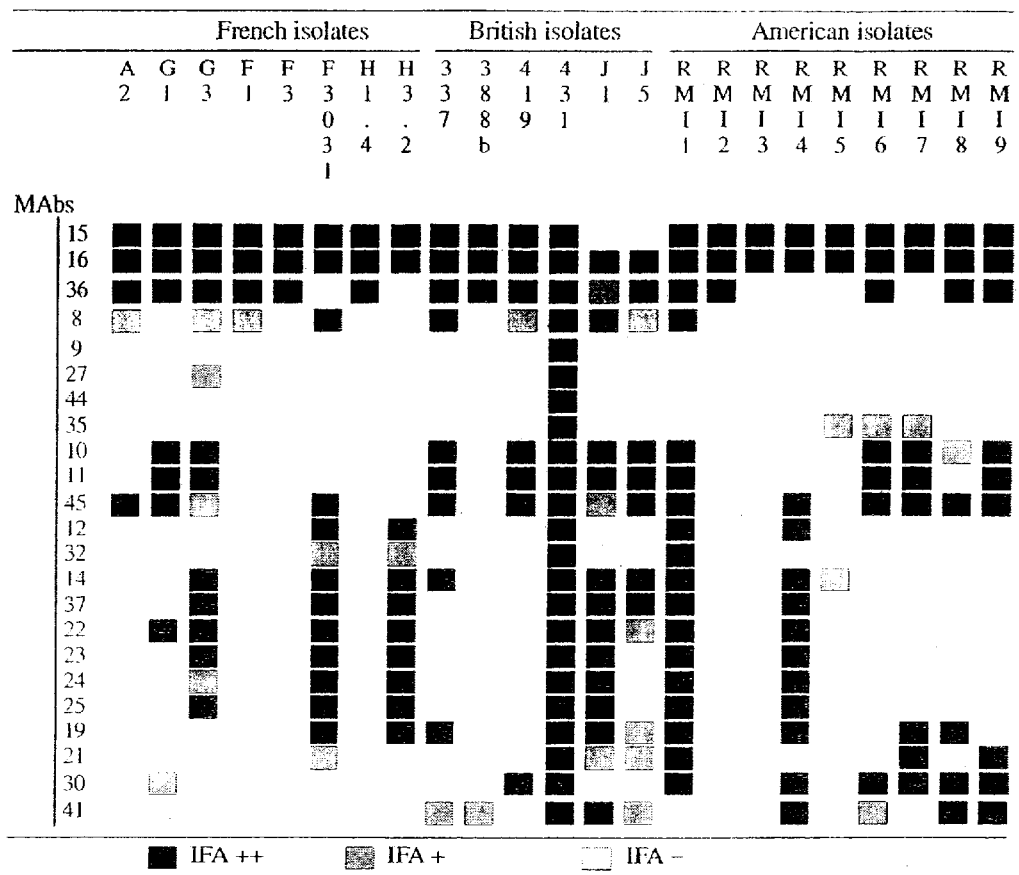
FIGURE 2: IFA PROFILES OF THE ISOLATES BY USING THE ANTI-P66 (FCV431) MONOCLONAL ANTIBODIES

INACTIVATED VACCINE AGAINST FELINE CALICIVIROSIS

RELATED APPLICATIONS

This application claims priority from French application no. 99 09420, filed Jul. 16, 1999, French application no. 00 01759, filed Feb. 11, 2000, and U.S. provisional application serial No. 60/193,197, filed Mar. 30, 2000. Each of the foregoing applications, patents and publications, and all documents cited or referenced therein ("application cited documents") and all documents cited or referenced in this specification ("herein cited documents") and all documents referenced or cited in herein cited documents and in application cited documents, including during the prosecution of any of the applications, patents, and application cited documents, are hereby incorporated herein by reference.

The present invention relates to the use of particular strains of feline caliciviruses for the production of immunogenic preparations and of vaccines, in particular inactivated or subunit vaccines, against feline calicivirosis. These immunogenic preparations and these vaccines may also be combined with immunogenic preparations or vaccines prepared on the basis of other feline pathogens, for the production of multivalent immunogenic preparations and vaccines.

Feline caliciviruses (FCV) were first described in 1957 (Fastier L. B. Am. J. Vet. Res. 1957. 18, 382–389). Feline caliciviruses are, with the feline herpesviruses, the two principal sources of viral diseases of the upper respiratory tract in cats. The FCV viruses affect a large number of animals, with FCV carrying rates of the order of 15 to 25%, and an anti-FCV seroprevalence of 70 to 100% (Coutts et al. Vet. Rec. 1994. 135. 555–556; Ellis T. M. Australian Vet. J. 1981. 57. 115–118; Harbour et al. Vet. Rec. 1991. 128. 77–80; Reubel et al. Feline Dendistry 1992. 22. 1347–1360). After an initial phase of hyperthermia, these respiratory diseases are generally accompanied by buccal ulcerations (palate, tongue, lips, nose), rhinitis, conjunctivitis, possibly anorexia and asthenia. The FCV viruses can also cause pneumonia, enteritis, and articular pain (lameness syndrome).

The FCV virus is transmitted only horizontally, there is no vertical transmission from the mother to its kitten during gestation (Johnson R. P. Res. Vet. Sci. 1984. 31. 114–119). FCV is transmitted by contact between infected animals and healthy animals or by the airways during sneezing (Wardley R C. Arch. Virol. 1976. 52. 243–249).

Feline caliciviruses are naked viruses of the Caliciviridae family, they possess a single-stranded positive RNA of about 7.7 kilobase pairs (kbp) in size (Radfor et al. Proc. $1^{st}$ Int. Symp. Caliciviruses ESVV 1997. 93–99).

Like many RNA viruses, a large heterogeneity exists within the viral population of FCV. The antigenic variations, demonstrated since the beginning of the 70s by cross-serum neutralization experiments, make it possible to classify the FCVs into several viral strains or quasispecies (Radford et al. Proc. $1^{st}$ Int. Symp. Caliciviruses ESVV 1997. 93–99).

Several FCV strains have been identified and isolated, in particular strain F9 (deposited with the American Type Culture Collection or ATCC under the accession number VR-782), strain 2280 (ATCC VR-2057), strain KCD (ATCC VR-651) and strain CFI (ATCC VR-654).

Vaccination against FCV was introduced since the end of the 70s from attenuated FCV strains, mainly strain F9 isolated in the USA in 1958 by Bittle (Bittle et al. Am. J. Vet. Res. 1960. 21. 547–550) or strains derived from F9 by passage in vitro or in vivo ("F9-like").

Inactivated vaccines are also available. They mainly use strains 255 and 2280, which were isolated in the USA respectively in 1970 in a cat with a pneumonia (Kahn and Gillepsie. Cornell Vet. 1970. 60. 669–683; Powvey et al. J. Am. Vet. Med. Assoc. 1980. 177. 347–350) and in 1983 in a cat suffering from lameness (Pedersen et al. Fel. Prac. 1983. 13. 26–35; Pedersen N. C. and Hawkins K. F. Vet Microbiol. 1995. 47. 141–156).

Because of antigenic drift over time, antisera produced against vaccine strains isolated in the 60–70s, such as strains F9, 255 or 2280, neutralize only few isolates of the 90s. For example, the anti-F9 serum neutralizes 43% of the American isolates of the period 1990–1996, against 56% for the period 1980–89 and 86% for the period 1958–79, and only 10% of the English isolates of the period 1990–96 (Lauritzen et al. Vet. Microbiol. 1997. 56. 55–63). Accordingly, attenuated and inactivated vaccines from old FCV strains at present no longer offer sufficient protection against recent FCV strains.

The objective of the present invention is the detection of new FCV strains, which induce in cats antibodies having a broad cross-neutralization spectrum.

Another objective of the invention is the production of immunogenic preparations and of vaccines against feline calicivirosis from these FCV strains.

Yet another objective of the invention is the production of multivalent immunogenic preparations and of multivalent vaccines against feline calicivirosis and against at least one other feline pathogen.

BRIEF DESCRIPTION OF THE DRAWINGS

FIG. 1 shows neutralizing titers obtained during cross-neutralizations; and,

FIG. 2 shows IFA profiles of isolates by using ant-p66 (FCV 431) monoclonal antibodies; monoclonal antibody 44 is specific to FCV 431.

The Applicant has selected four FCV strains obtained by pharyngeal swabs taken in France, the United Kingdom and the USA on cats exhibiting signs of infection by feline calicivirus. They are respectively strain G1 (deposited at the Collection Nationale de Cultures de Microorganismes (or CNCM) of the Institut Pasteur, 28, rue du Dr Roux, 75724 Paris Cedex 15, France, under the accession number I-2167) and strain 431 (deposited at the CNCM under the accession number I-2166), both deposited on Mar. 12, 1999 under the terms of the Budapest Treaty. The latter two strains are American and designated RMI6 and RMI9. The FCV G1 strain isolated in France does not correspond to the FCV strain isolated in the United Kingdom in 1978 by Tohya Y. (Tohya Y. et al. Jpn. J. Sci., 1990, 52, 955–961) and also called G1.

The selection of the FCV 431, G1, RMI6 and RMI9 strains was carried out by cross-serum neutralization tests with respect to the FCV isolates of a reference panel. This reference panel is composed of 18 current isolates of FCV taken from cats exhibiting signs of infection with feline calicivirus and coming from three distinct geographical regions. 7 isolates are American, these isolates are identified RMI1, RMI2, RMI3, RMI5, RMI6, RMI7 and RMI9. 7 isolates are French, they are designated A2, F1, G1, G3, F3031, H3-2 and H1-4. The last 4 isolates are English, they are designated 431, 388b, 337 and J5.

The panel strains and the RMI6 and RMI9 strains are accessible from the Applicant simply on request.

They have also been published in a review article "Archives of Virology" (Poulet et al. Arch. Virol. February 2000. 145(2). 243–261), available online on Internet on the date of filing with the editor.

During cross-serum neutralization tests between the 18 FCV isolates of the reference panel, it was found, surprisingly, that the antiserum for isolate 431 neutralizes 14 of the 17 heterologous isolates of the reference panel (the homologous serum neutralization titer is not taken into account). By comparison, the antisera for the "historical" vaccine strains 255 and F9 neutralize only 2 of the 18 panel isolates each.

Unexpectedly, the Applicant has therefore found with the FCV 431 strain a dominant strain which can be used for the protection of the Felidae and in particular of cats against most FCV strains. By virtue of the panel of FCV strains disclosed here, it is possible for persons skilled in the art to select other dominant FCV strains. By way of equivalence, the invention also covers through the FCV 431 strain the FCV strains which are equivalent thereto, which have antibodies with broad cross-neutralization spectrum.

Equivalence exists when the antiserum for an FCV strain seroneutralizes at least 13 of the 18 heterologous isolates of the reference panel (that is to say including FCV 431), preferably when it seroneutralizes at least 14 of the 18 heterologous isolates of the reference panel, still more preferably when it seroneutralizes at least 15 of the 18 heterologous isolates of the reference panel.

It is generally considered that an FCV strain seroneutralizes another FCV strain when the heterologous serum neutralization titer is greater than or equal to $1.2 \log_{10} VN_{50}$ (Povey C. and Ingersoll J., Infection and Immunity, 1975, 11, 877–885). The Applicant took this value as the positivity threshold. However, the cross-serum neutralization results obtained with an FCV isolate having a homologous serum neutralization titer of less than or equal to $2 \log_{10} VN_{50}$ cannot be interpreted.

A second method for establishing the equivalence of an FCV strain with respect to the FCV 431 strain is to use monoclonal antibodies specific for the FCV 431 strain and to test the candidate FCV strain by indirect immunofluroescence (IIF). The Applicant has thus succeeded in producing several monoclonal antibodies which have proved specific for 4312, for example with the monoclonal antibody 44. This monoclonal antibody and the corresponding hybridoma are available from the Applicant upon simple request and are also disclosed in the article by Poulet et al. Arch. Virol. 2000. 145. 1–19. The corresponding hybridoma was also deposited on Aug. 11, 1999 under the terms of the Budapest Treaty at the CNCM under the accession number I-2282. It goes without saying, however, that persons skilled in the art are perfectly capable of producing monoclonal antibodies by conventional techniques and of selecting, relative to the panel, those which are specific for the 431 strain.

The first subject of the present invention is therefore immunogenic preparations and vaccines prepared from feline calicivirus strain 431, which includes its equivalents as defined above, preferably in inactivated or subunit form, in a veterinarily acceptable vehicle or excipient, and preferably in the presence of an adjuvant. The notion of immunogenic preparation covers here any preparation capable, once administered to cats, of inducing an immune response directed against the feline pathogen considered. Vaccine is understood to mean a preparation capable of inducing effective protection.

The other FCV G1, RMI6 and RMI9 strains were chosen for their complementarity to the FCV 431 strain, namely that the combination of the antisera for 431 and for one of these three FCVs seroneutralize 100% of the isolates of the reference panel, that is to say that these three FCV strains have a homologous serum neutralization titer greater than or equal to $2 \log_{10} VN_{50}$ and heterologous serum neutralization titers greater than or equal to $1.2 \log_{10} VN_{50}$ with respect to the FCV isolates of the reference panel against which the 431 antiserum does not seroneutralize or seroneutralizes weakly (value less than $1.2 \log_{10} VN_{50}$). The invention also covers the equivalent FCV strains having the same complementarity with respect to the FCV 431 strain. It is also possible to produce and select monoclonal antibodies specific for these strains, in particular for G1, which makes it possible to determine equivalents on this other basis.

The second subject of the invention is therefore immunogenic preparations and vaccines comprising, in addition to the antigens of the FCV 431 strain or one of its equivalents according to the invention, antigens of at least one other FCV strain, especially a complementary strain, in particular chosen from the group comprising G1, RMI6, RMI9, which includes their equivalents, in a veterinarily acceptable vehicle or excipient, and optionally an adjuvant. Preferably, the antigens obtained from the other FCV strain(s) comprise inactivated virus or subunits.

The subject of the invention is in particular the combination of the two FCV 431 and G1 strains for the production of immunogenic preparations or of inactivated or subunit vaccines.

Surprisingly, the combination of the two FCV G1 and 431 strains causes advantageously a synergistic effect. During studies on the complementarity of the FCV G1 and 431 strains, the immune responses induced by G1 alone, 431 alone or the combination of both (G1+431) were compared. The group of animals which were immunized with the combination of the two FCV G1 and 431 strains had the benefit of a better clinical protection.

The culture and propagation of the FCV viruses is preferably carried out on feline cells, more particularly on Crandell-Reese Feline Kidney or CRFK cells (accessible from the American Type Culture Collection under the number CCL-94) with a multiplicity of infection (moi) of 2 to 0.01 cell culture infectious doses 50% ($CCID_{50}$) per cell, preferably 0.5 $CCID_{50}$/cell.

After harvesting and clarifying, the FCV viruses intended to produce an inactivated immunogenic preparation or an inactivated vaccine are inactivated by a chemical treatment (e.g. formalin or formaldehyde, β-propiolactone, ethylenimine, binary ethylenimine (BEI)) and/or a heat treatment. Preferably, the viruses according to the invention are inactivated by the action of ethylenimine formed immediately before use from bromoethylamine (BEA). The viral particles may be concentrated by conventional concentration techniques, in particular by ultrafiltration and then optionally purified by conventional purification means, in particular gel filtration techniques or selective precipitation techniques in particular in the presence of polyethylene glycol (PEG). A purification without previous concentration can also be done.

For the production of an immunogenic preparation or of an inactivated or subunit vaccine, the viral particles are taken up in a veterinarily acceptable vehicle or excipient, and optionally supplemented with an adjuvant. The quantity of antigen is in particular equal to a preinactivation titer of about $10^5$ to about $10^{10}$ $CCID_{50}$ per dose, preferably of about $10^8$ to about $10^9$ $CCID_{50}$ per dose.

To supplement the immunogenic preparations and vaccines according to the invention with adjuvants, it is possible to use as adjuvant (1) aluminum hydroxide, (2) a polymer of acrylic or methacrylic acid, a polymer of maleic anhydride and of alkenyl derivative, or (3) to formulate the immunogenic preparation or vaccine in the form of an oil-in-water emulsion, in particular the emulsion SPT described p 147 "Vaccine Design, The Subunit and Adjuvant Approach" edited by M. Powell, M. Newman, Plenum Press 1995, and the emulsion MF59 described p 183 in the same book.

The oil-in-water emulsion may in particular be based on light liquid paraffin oil (European Pharmacopeia type); isoprenoid oil such as squalane, squalene; oil resulting from the oligomerization of alkenes, in particular of isobutene or of decene; esters of acids or alcohols containing a linear alkyl group, more particularly vegetable oils, ethyl oleate, propylene glycol di(caprylate/caprate), glyceryl tri (caprylate/caprate), propylene glycol dioleate; esters of branched fatty alcohols or acids, in particular esters of isostearic acid. The oil is used in combination with emulsifiers to form the emulsion. The emulsifiers are preferably nonionic surfactants, in particular the esters of sorbitan, mannide, glycerol, polyglycerol, propylene glycol and of oleic, isostearic, ricinoleic or hydroxystearic acid, which are optionally ethoxylated, the polyoxypropylene-polyoxyethylene block copolymers, in particular the Pluronic® copolymers, especially L121.

The polymers of acrylic or methacrylic acid are crosslinked, in particular with polyalkenyl ethers of sugars or polyalcohols. These compounds are known under the term carbomer (Pharmeuropa vol. 8, No. 2, June 1996). Persons skilled in the art can also refer to U.S. Pat. No. 2,909,462 (incorporated by way of reference) describing such acrylic polymers crosslinked with a polyhydroxylated compound having at least 3 hydroxyl groups, preferably not more than 8, the hydrogen atoms of at least three hydroxyls being replaced with unsaturated aliphatic radicals having at least 2 carbon atoms. The preferred radicals are those containing 2 to 4 carbon atoms, e.g. vinyls, allyls and other ethylenically unsaturated groups. The unsaturated radicals may themselves contain other substituents, such as methyl. The products sold under the name Carbopol® (BF Goodrich, Ohio, USA) are particularly appropriate. They are crosslinked with an allyl sucrose or with allylpentaerythritol. Among them, there may be mentioned Carbopol® 974P, 934P and 971P.

Among the copolymers of maleic anhydride and of alkenyl derivative, the EMA® copolymers (Monsanto) which are copolymers of maleic anhydride and of ethylene, which are linear or crosslinked, for example crosslinked with divinyl ether, are preferred. Reference may be made to J. Fields et al., Nature, 186: 778–780, Jun. 4, 1960 (incorporated by way of reference). From the point of view of their structure, the polymers of acrylic or methacrylic acid and the EMA® copolymers are preferably formed of basic units of the following formula:

$$----\overset{\overset{\displaystyle R_1}{|}}{\underset{\underset{\displaystyle COOH}{|}}{C}}-(CH_2)_x-\overset{\overset{\displaystyle R_2}{|}}{\underset{\underset{\displaystyle COOH}{|}}{C}}-(CH_2)_y----$$

in which:
$R_1$ and $R_2$, which are identical or different, represent H or $CH_3$
x=0 or 1, preferably x=1
y=1 or 2, with x+y=2

For the EMA® copolymers, x=0 and y=2. For the carbomers, x=y=1.

The concentration of polymer in the final vaccine composition will be from 0.01% to 1.5% W/V, more particularly from 0.05 to 1% W/V, preferably from 0.1 to 0.4% W/V.

It is of course possible to also combine inactivated virus and subunits of the same FCV strain in accordance with the invention and/or of different FCV strains in accordance with the invention.

The subject of the invention is also a multivalent vaccine comprising one inactivated feline calicivirus valency, comprising at least the FCV 431 strain, which includes its equivalents, and optionally at least one other FCV strain, in particular a strain which is complementary within the meaning of the invention, in particular chosen from G1, RMI6 and RMI9, and at least one valency for another feline pathogen, in a veterinarily acceptable vehicle or excipient and preferably with an adjuvant, in particular one of those described above. It is likewise possible to produce subunit-based multivalent vaccines.

Said feline pathogens are in particular chosen from the group comprising the feline rhinotrachitis virus or the feline herpesvirus (FHV), the feline leukemia virus (FeLV), feline panleukopenia virus or feline parvovirus (FPV), the feline infectious peritonitis virus (FIPV), the feline immunodeficiency virus (FIV), the rabies virus, Chlamydia.

The FCV vaccines according to the invention may be mixed immediately before use with the other feline valency (valencies) which may be in the form of attenuated live, inactivated, subunit, recombinant or polynucleotide vaccines.

The subject of the invention is therefore also a multivalent vaccination kit or box comprising, packaged separately, an FCV valency according to the invention in a veterinarily acceptable vehicle or excipient, and preferably with an adjuvant, and at least one valency of another feline pathogen. The FCV valency can serve as solvent for another feline valency, in particular attenuated, recombinant or polynucleotide valency provided in freeze-dried form.

In accordance with a feature of the invention, it is possible to produce immunogenic preparations or subunit vaccines, by extraction of the capsid from the virus, with optionally inactivation before or after the extraction. These preparations and vaccines therefore comprise, as sole active ingredient or otherwise, such a product of extraction containing predominantly capsid protein and optionally subfragments, optionally inactivated, produced from the strains according to the invention, in particular strain 431, which includes its equivalents, optionally also from another FCV strain, in particular G1 or equivalents. These subunit vaccines and preparations are advantageously supplemented with adjuvant, for example as described supra. It is also possible to mix whole inactivated vaccine or preparation and subunit vaccine or preparation.

The subject of the invention is also an immunogenic preparation or a vaccine based on the G1 strain, in particular which is inactivated or a subunit of extraction.

The subject of the invention is also a method of immunizing cats against diseases caused by the feline caliciviruses.

This method of immunization comprises the administration of a combined multivalent, subunit or inactivated FCV vaccine according to the invention to cats. The administration of said vaccine may be carried out in particular by the parenteral route, preferably by the subcutaneous or intramuscular route.

Persons skilled in the art have the competence necessary to define precisely the number of injections and the doses of each vaccine to be used for each vaccination protocol.

The dose volumes may be in particular between 0.2 and 2 ml, preferably of the order of 1 ml.

The invention will now be described in greater detail with the aid of the embodiments taken by way of nonlimiting examples and referring to the single figure, giving a table of the cross-serum neutralization titers.

EXAMPLES

Example 1

Viral Isolates and Hybridomas

The feline caliciviruses (FCV) were obtained by pharyngeal swabs taken on cats exhibiting signs of infection with feline caliciviruses. These FCVs have different geographical origins.

The FCV 431, 337, J5, 388b, 220 and 393 strains were isolated in Great Britain and provided by Professor O. Jarrett of the University of Glasgow, UK.

The FCV A2, G1, G3, F3031, F1, H3-2 and H1-4 strains were isolated in France by the Applicant.

The FCV RMI1, RMI2, RMI3, RMI5, RMI6, RMI7 and FMI9 strains were isolated in the USA by the Applicant.

The pharyngeal samples were collected in 2 ml of Dulbecco's modified Eagle's minimum medium (DMEM, Gibco BRL), supplemented with 5% fetal calf serum (Bayer Diagnostic), with antibiotics, more particularly with 50 mg/l of gentamycin. Each isolate is frozen at −70° C. while waiting to be tested. The monoclonal antibody 44, obtained from the hybridoma identified 431 2 0 17 E9 T, is specific for the FCV 431 strain.

Example 2

Amplification of the Viral Isolates

Cells of the cat kidney line (Crandell-Reese Feline Kidney or CRFK No. ATCC CCL-94, Crandell et al. In Vitro 1973. 9. 176–185) are cultured in a 96-well plate or in a 25-cm$^2$ Falcon (Falcon) with DMEM medium supplemented with 5% fetal calf serum, containing about 100,000 cells per ml. The cells are cultured at 37° C. in an atmosphere containing 5% $CO_2$. After 3 days, the cell layer arrives at confluence. The culture medium is then replaced with serum-free DMEM medium supplemented with 50 mg/l of gentamycin and the thawed aliquote of the FCV viral isolates (Example 1) are added at the rate of a volume of 100 μl of four-fold serial dilutions per well for the limiting dilution cloning of the FCV viruses or of 1 ml per Falcon.

When the cytopathic effect (ECP) is complete (24–48 hours after the start of the culture), the viral suspensions are harvested and frozen at −70° C. 3 to 4 successive passages are generally necessary for the production of a viral batch. The viral batch is stored at −70° C.

Example 3

Production of Serum

For each FCV virus, an antiserum was produced by inoculating kittens by the oronasal route with $10^{6.0}$ $CCID_{50}$ of the relevant FCV virus. The specific pathogen-free (SPF) kittens were 10 to 14 weeks old. The serum of each animal was collected one month after the infection. The sera were heat-inactivated (30 minutes at 56° C.), distributed, aliquoted and stored at −20° C.

Example 4

Cross-serum Neutralization in Vitro

Cross-serum neutralization tests were carried out between 18 field isolates obtained by pharyngeal swabs performed on cats exhibiting signs of feline calicivirosis. 7 of them have as geographical origin France, they are the isolates identified A2, F3031, G1, G3, F1, H3-2 and H1-4. 4 have as geographical origin Great Britain, they are the isolates identified J5, 337, 388b and 431. Finally, 7 have as geographical origin the USA, they are the isolates identified RMI1, RMI2, RMI3, RMI5, RMI6, RMI7 and RMI9.

The serum obtained for each isolate (Example 3) was tested for its ability to neutralize the 18 isolates. The sera were three-fold serially diluted with DMEM medium in 96-well cell culture plates. 0.05 ml of culture medium containing approximately 100 $CCID_{50}$ of the selected viral strain was added to 0.05 ml of the dilute serum produced as in Example 2. This mixture was incubated for 2 hours at 37° C. in an incubator under an atmosphere containing 5% $CO_2$.

0.15 ml of a suspension of CRFK cells containing about 100,000 cells per ml was then added to each mixture. The cytopathic effect was observed by phase contrast microscopy after 4 days of culture at 37° C in an atmosphere containing 5% $CO_2$. The neutralizing titers of each serum were calculated according to the Kärber method. The titers are given in the form of the highest dilution inhibiting the cytopathic effect for 50% of the wells. The titers are expressed in $\log_{10}$. The minimum titer thus found was 0.7 $\log_{10}$ $VN_{50}$. Each serum was titrated at least twice, preferably three times.

FIG. 1 gives all the neutralizing titers obtained during cross-serum neutralizations carried out between these 18 FCV strains and these 18 sera.

Example 5

Indirect Immunofluorescence (IIF) Tests

The IIF tests are carried out on 96-well plates containing the CRFK cells cultured in monolayers infected with the FCV viruses to be tested.

200 $\mu$l per well of a suspension of CRFK cells containing 90,000 cells/ml in F15 medium (Gibco BRL, Cat #045-1075) containing 5% fetal calf serum are cultured in a 96-well plate. At confluence, 320 CCID50 of FCV are inoculated in 100 $\mu$l of F15 medium. When the first CPE foci appear, the cells are then rinsed with cold PBS with no calcium or magnesium (PBS, Sigma), and then fixed at −20° C. for 30 minutes with cold acetone containing 5% v/v of water. After drying, the infected and fixed cells are brought into contact for 30 minutes at 37° C. with 100 $\mu$l per well of ascitic fluid corresponding to the anti-FCV 431 monoclonal antibody 44 (hybridoma 431 2 0 17 E9 T, diluted 1/5000 approximately in 50 mM TRIS-HCl buffer, pH 7.6.

After two rinses in PBS, the attachment of the antibodies is visualized by incubation under the same conditions of a goat anti-mouse IgG antibody conjugated with fluorescein isothianate (Biosys, FITC conjugated at 2 mg/ml) and diluted 1/150 in 50 mM TRIS-HCl buffer, pH 7.6. The reading is made under an optical microscope under UV light.

This monoclonal antibody was tested with respect to each of the isolates of the panel. It is attached exclusively to the CRFK cells infected with FCV 431.

This test may be used to determine the equivalents of the FCV 431 strain. These equivalents are those to which the monoclonal antibody 44 attaches.

It is noted that monoclonal 44 is a neutralizing and conformational antibody and that neutralization is correlated with protection. And FIG. 2 shows IFA profiles of isolates by using ant-p66 (FCV 431) monoclonal antibodies; monoclonal antibody 44 is specific to FCV 431.

Example 6

Synergy 32 nonvaccinated SPF kittens about 9 weeks old are divided by randomization into 4 groups (identified from A to D) of 8 kittens each, each group is housed in an isolated box.

After thawing the viral suspensions (Example 2) and diluting in PBS so as to obtain the desired titer, the cats are vaccinated by subcutaneous injection of 1 ml of FCV G1 inoculum at $10^{3.3}$ $CCID_{50}$/ml for group B, of 1 ml of FCV 431 inoculum at $10^{3.5}$ $CCID_{50}$/ml for group C, of 0.5 ml of FCV G1 inoculum at $10^{3.3}$ $CCID_{50}$/ml and 0.5 ml of FCV 431 inoculum at $10^{3.5}$ $CCID_{50}$/ml (at a different injection site) for group D. Group A serves as control group.

Half of each group A to D is randomly distributed into two groups 1 and 2 and housed in separate boxes. The animals are challenged on the 31st day after vaccination (d31).

The animals in group 1 are challenged by administration of 1 ml of challenge viral strain FCV 220 having a titer of $10^{7.2}$ CCID$_{50}$/ml by the oronasal route (0.5 ml by the oral route and 0.25 ml into each nostril).

The animals in group 2 are challenged by administration of 1 ml of challenge viral strain FCV 393 having a titer of $10^{6.8}$ CCID$_{50}$/ml by the oronasal route (0.5 ml by the oral route and 0.25 ml into each nostril).

The virulent strains FCV 220 and 393 were chosen because they are distant in cross-serum neutralization from the viral strains FCV G1 and 431.

Any cross-contamination between the two boxes is carefully avoided. Clinical monitoring of the animals in both groups is done by taking the rectal temperature and clinical examinations of the animals (general state, presence of ulcers of the tongue and of the palate, presence of gingivitis, presence of rhinitis, presence of conjunctivitis, presence of lameness, death of the animal).

The total clinical score for each animal was calculated by adding the scores obtained for each group of clinical signs according to the following scale:

rectal temperature:
    0—less than 39° C.
        1—greater than or equal to 39° C. and less than 39.5° C.
        2—greater than or equal to 39.5° C. and less than 40° C.
        3—greater than or equal to 40° C.
general state:
    0—normal behavior
    1—exhaustion
ulcers of the tongue and of the palate (some of the diameters of all the ulcers, if there are several):
    0—absence of ulcer
    1—diameter of 1 to 5 mm
    2—diameter of 6 to 10 mm
    3—diameter greater than 10 mm
gingivitis:
    0—absence of gingivitis
    1—gingivitis
rhinitis:
    0—absence of rhinitis
    1—rhinitis with serous nasal discharge
    2—rhinitis with mucous to mucopurulent nasal discharge
conjunctivitis:
    0—absence of conjunctivitis
    1—conjunctivitis with serous discharge
    2—conjunctivitis with mucopurulent discharge
lameness:
    0—absence of lameness
    1—lameness
death:
    0—survival
    5—death.

The mean clinical scores obtained are the following:

| Group/challenge | FCV 220 | FCV 393 |
| --- | --- | --- |
| Control (group A) | 31 | 30 |
| FCV G1 (group B) | 5 | 23 |
| FCV 431 (group C) | 6 | 18 |
| FCV G1 + FCV 431 (group D) | 2 | 9 |

The results thus obtained show synergy between the FCV G1 and FCV 431 strains by a significant difference between the mean value obtained for the best strains and that obtained for the combination of the two strains (Kruskal-Wallis test).

Example 7

Production of Inactivated Vaccine

The CRFK cells are cultured at 37° C. in 2-liter roller flasks (850 $cm^2$) in modified Eagle's medium (MEM, Gibco BRL) supplemented with 2.5% of lactalbumin hydrolysate (Gibco BRL) and 5% fetal calf serum (Gibco BRL). 300 ml of a cellular suspension in MEM medium containing about 100,000 cells/ml are added per roller flask. After 3 days, the cell layer becomes confluent. The cell culture medium is then replaced with serum-free MEM and the FCV virus added at a multiplicity of infection (moi) of 0.5 $CCID_{50}$/cell. The viral culture is maintained at 37° C. for 24 to 48 hours until a cytopathic effect is obtained for the whole cellular lawn. The viral suspension is harvested and then clarified on a bag filter having a porosity of 1.5 μm. The FCV virus titer at harvest is 8.5 +/−0.3 log10 $CCID_{50}$/ml.

The virus is inactivated with ethylenimine at the concentration of about 8 mM at 22° C. for 18 hours.

The ethylenimine is prepared immediately before use by dissolving 28 g of sodium hydroxide pellets in 200 ml of distilled water and adding 68.1 g of bromoethylamine (BEA) corresponding to a 1.2 M solution approximately (H. Bahnemann, Arch. Virol., 1975, 47, 47–56). The inactivated viral suspension is concentrated 100-fold on an Ultrasette-type ultrafiltration cartridge with a cut-off of 100 kDa (Filtron) and then frozen at −70° C.

The inactivated viral suspension after thawing is diluted 1/33 in PBS buffer (NaCl 8 g/l; KCl 0.2 g/l; $KH_2PO_4$ 0.2 g/l; $Na_2HPO_4$, 2 $H_2O$ 1.44 g/l). The vaccine is prepared in the same manner: 167 ml of aqueous phase consisting of the dilution of the inactivated virus are emulsified in 83 ml of an oily phase containing 7% w/v of anhydromannitol oleate, 8% w/v of ethoxylated oleic acid containing 11 molecules of ethylene oxide (EO) on average and 85% v/v of light liquid paraffin oil (European Pharmacopeia type) with the aid of a Silverson turbine emulsifier at 32° C. for 2 minutes. The vaccine is then stored at 5° C.

An alternative method for preparing the vaccine consists in forming into an emulsion by three passes through a model Y110 high-pressure homogenizer (Microfluidics Corp.) at a pressure of 600 bar and a temperature of between 30 and 40° C. the mixture 5% w/v squalane, 2.5% w/v Pluronic® L121, 0.2% w/v Tween 80, 92.3% v/v of inactivated viral suspension diluted 1/46 in PBS buffer after thawing. The vaccine is then stored at 5° C.

Another alternative method consists in preparing a solution containing 0.4% w/v of Carbopol® 974P in physiological saline (NaCl 9 g/l). The pH is adjusted to 7.3–7.4 with sodium hydroxide. This solution of Carbopol is then mixed in equal parts with the suspension of inactivated FCV virus diluted 1/25 after thawing. The vaccine is then stored at 5° C.

The aqueous phase of the emulsions or the aqueous phase mixed with Carbopol® consists of a dilution in PBS of the concentrated inactivated viral suspension corresponding either to the FCV 431 strain or to the FCV G1 strain or a mixture in equal parts of the FCV 431 and G1 strains.

Example 8

Control of the Immunogenicity of Inactivated FCV 431

19 nonvaccinated SPF kittens about 9 weeks old are divided by randomization into 2 groups (identified from A and B), the first with 12 kittens and the second with 7 kittens, each group is housed in an isolated box.

The vaccine is prepared with the adjuvant composed of anhydromannitol oleate, ethoxylated oleic acid and light liquid paraffin oil as described in Example 7.

The cats are vaccinated twice (D0 and D28) by subcutaneous injection of 1 ml of FCV 431 inoculum at $10^7$ CCID$_{50}$/ml for group A. Group B serves as control group.

The animals are challenged on the $42^{nd}$ day after the first vaccination (D42) by administration of 1 ml of challenge viral strain FCV 431 having a titer of $10^6$ CCID$_{50}$/ml by the oronasal route (0.5 ml by the oral route and 0.25 ml into each nostril).

The level of anti-FCV 431 neutralizing antibodies and the clinical score were monitored. The total clinical score for each animal was calculated by adding the scores obtained for each group of clinical signs according to the scale given in Example 6.

The results obtained are the following:

Anti-FCV 431 neutralizing antibody titers expressed as $\log_{10}$ VN$_{50}$/ml:

| Group | Antibody on D0 | Antibody on D28 | Antibody on D42 |
| --- | --- | --- | --- |
| FCV 431 vaccine (group A) | 0.24 | 1.61 | 2.87 |
| Controls (group B) | 0.24 | 0.24 | 0.24 |

Mean clinical scores over the period D42 to D56:

| Group | Clinical score |
| --- | --- |
| FCV 431 vaccine (group A) | 0.7 |
| Controls (group B) | 33.7 |

These results show an excellent clinical protection against the homologous challenge and good seroconversion.

It should be clearly understood that the invention defined by the appended claims is not limited to the specific embodiments indicated in the description above, but encompasses the variants which do not depart from the scope or the spirit of the present invention.

What is claimed is:

1. An immunogenic composition comprising a veterinarily acceptable vehicle or excipient and an isolated feline calicivirus that binds to monoclonal antibody 44, secreted by the hybridoma deposited at the CNCM under accession number I-2282.

2. The immunogenic composition of claim 1 wherein the FCV is inactivated.

3. An immunogenic composition comprising a veterinarily acceptable vehicle or excipient and an isolated feline caliciviras strain 431 deposited at the CNCM under accession number I-2166.

4. The immunogenic composition of claim 3 additionally comprising a FCV strain G1 deposited at the CNCM under accession number I-2167.

5. The immunogenic composition of claim 3 wherein the FCV is inactivated.

6. The immunogenic composition of claim 4 wherein the FCV is inactivated.

7. The immunogenic composition of claim 5 which is a vaccine.

8. The immunogenic composition of claim 6 which is a vaccine.

9. The immunogenic composition of any one of claims 1–8 additionally comprising an adjuvant.

10. The immunogenic composition of claim 9 wherein the adjuvant comprises aluminum hydroxide or a polymer of acrylic or methacrylic acid or a polymer of maleic anhydride.

11. The immunogenic composition of claim 9 wherein the adjuvant comprises a carbomer.

* * * * *

UNITED STATES PATENT AND TRADEMARK OFFICE
CERTIFICATE OF CORRECTION

PATENT NO.    : 6,534,066 B1
DATED         : March 18, 2003
INVENTOR(S)   : Herve Poulet et al.

It is certified that error appears in the above-identified patent and that said Letters Patent is hereby corrected as shown below:

<u>Title page,</u>
Item [75], Inventors, change "Lyons" to -- Lyon --.

Item [73], Assignee, change "Lyons" to -- Lyon --.

<u>Column 12,</u>
Line 16, change "caliciviras" to -- calicivirus --.

Signed and Sealed this

Fifteenth Day of July, 2003

JAMES E. ROGAN
*Director of the United States Patent and Trademark Office*